United States Patent
Steiner Vanha et al.

(10) Patent No.: US 12,231,833 B2
(45) Date of Patent: Feb. 18, 2025

(54) SENSOR MODULE (71) Applicant: SENSIRION AG, Stäfa (CH)

(72) Inventors: Ralph Steiner Vanha, Stäfa (CH); Samuel Fuhrer, Stäfa (CH); Marcel Pluess, Stäfa (CH); Ulrich Bartsch, Stäfa (CH)

(73) Assignee: SENSIRION AG, Stäfa (CH)

( * ) Notice: Subject to any disclaimer, the term of this patent is extended or adjusted under 35 U.S.C. 154(b) by 1113 days.

(21) Appl. No.: 16/979,826

(22) PCT Filed: Feb. 28, 2019

(86) PCT No.: PCT/EP2019/055019
§ 371 (c)(1),
(2) Date: Sep. 10, 2020

(87) PCT Pub. No.: WO2019/174925
PCT Pub. Date: Sep. 19, 2019

(65) Prior Publication Data
US 2021/0044877 A1 Feb. 11, 2021

(30) Foreign Application Priority Data
Mar. 12, 2018 (EP) .................................. 18161279

(51) Int. Cl.
*H04Q 9/00* (2006.01)
*G01N 33/00* (2006.01)
(Continued)

(52) U.S. Cl.
CPC ........... *H04Q 9/00* (2013.01); *G01N 33/0022* (2013.01); *G01N 33/0036* (2013.01);
(Continued)

(58) Field of Classification Search
CPC .. H04Q 9/00; G01N 33/0022; G01N 33/0036; G01N 33/0073; G06F 1/04; G06F 13/40
See application file for complete search history.

(56) References Cited

U.S. PATENT DOCUMENTS 6,134,485 A 10/2000 Taniellan et al.
7,112,774 B2 * 9/2006 Baer .................... H04N 13/296
348/42
(Continued)

FOREIGN PATENT DOCUMENTS

CN 103278196 A 9/2013
CN 104678912 A 6/2015
(Continued)

OTHER PUBLICATIONS

Lee et al., "A Sensor-Fusion Solution for Mobile Health-Care Applications" in Smart Sensor Systems, Springer 2015 (Year: 2015).*
(Continued)

*Primary Examiner* — Douglas Kay
(74) *Attorney, Agent, or Firm* — Mannava & Kang, P.C (57) ABSTRACT

A sensor module comprises a master sensor unit for sensing a first environmental parameter, a slave sensor unit for sensing a second environmental parameter, a common substrate on which the master sensor unit and the slave sensor unit are mounted, and a digital bus interface for a communication between the master sensor unit and the slave sensor unit. The master sensor unit comprises a non-volatile memory for storing calibration data and configuration data of the master sensor unit and the slave sensor unit. The master sensor unit is embodied as a first chip, and the slave sensor unit is embodied as a second chip. Such sensor module is compact, robust and versatile.

18 Claims, 3 Drawing Sheets

(51) Int. Cl.
*G06F 1/04* (2006.01)
*G06F 13/40* (2006.01)

(52) U.S. Cl.
CPC ........... *G01N 33/0073* (2013.01); *G06F 1/04* (2013.01); *G06F 13/40* (2013.01); *H04Q 2209/30* (2013.01)

(56) References Cited

U.S. PATENT DOCUMENTS

| | | | | |
|---|---|---|---|---|
| 8,291,143 | B1* | 10/2012 | Moobed | G06F 13/4295 |
| | | | | 713/400 |
| 10,289,594 | B2* | 5/2019 | Harpak | G06F 1/10 |
| 2005/0077450 | A1* | 4/2005 | Baer | H04N 13/239 |
| | | | | 348/E13.025 |
| 2009/0022255 | A1* | 1/2009 | Kanekawa | G06F 13/4291 |
| | | | | 375/356 |
| 2010/0211336 | A1* | 8/2010 | Madrid | H01L 25/065 |
| | | | | 702/57 |
| 2015/0151960 | A1 | 6/2015 | Mc Cleland et al. | |
| 2018/0189212 | A1* | 7/2018 | Harpak | G06F 1/10 |
| 2020/0370741 | A1* | 11/2020 | Hutson | H05B 47/105 |

FOREIGN PATENT DOCUMENTS

| | | |
|---|---|---|
| CN | 107743054 A | 2/2018 |
| WO | WO-2016/203356 | 12/2016 |

OTHER PUBLICATIONS

Lee et al., "A Sensor-Fusion Solution for Mobile Health-Care Applications", Chapter in Smart Sensors and Systems, Springer 2015, pp. 387-397 (Year: 2015).*
Chen-Yi Lee, et al., "A Sensor-Fusion Solution for Mobile Health-Care Applications", Jan. 1, 2015, 12 pages.
Bosch "Low power gas, pressure, temperature & humidity sensor", BME680, pp. 50.
International Search Report and Written Opinion dated Jun. 26, 2019, PCT Patent Application No. PCT/EP2019/055019, filed Feb. 28, 2019, European Patent Office, 10 pages.

* cited by examiner

SENSOR MODULE

CLAIM FOR PRIORITY

The present application is a national stage filing under 35 U.S.C 371 of PCT application number PCT/EP2019/055019, having an international filing date of Feb. 28, 2019, which claims priority to European patent application number 18161279.7 having a filing date of Mar. 12, 2018, the disclosures of which are hereby incorporated by reference in their entireties.

TECHNICAL FIELD

The present invention relates to a sensor module.

BACKGROUND ART

It is desired that a sensor module senses not only one, but a variety of environmental parameters, such as at least two quantities e.g. out of relative humidity, temperature, gas concentration or aerosol concentration. To achieve this goal, several separate sensors are routinely connected to and controlled by a central control unit representing a physical entity separate and possibly arranged remote from the sensors. However, such set-up results in large and interference-prone sensor arrangements.

An approach yielding a more compact device is combining the different sensors on a single chip. However, such combination brings about difficulties due to different working principles and/or working conditions of and/or different manufacturing processes for the different sensors. For instance, MOX gas sensors require a heater for heating a sensitive element, whereas heat produced by the heater corrupts measurements e.g. of a temperature sensor. Or, a MOX gas sensors may be less suitable for CMOS co-integration together with other sensors. Hence, developing a compact sensor module with different sensors on a single chip can be expensive and complex.

DISCLOSURE OF THE INVENTION

The problem to be solved by the present invention is to provide a sensor module for sensing different environmental parameters, which overcomes the disadvantages and limitations of the existing sensor devices.

The problem is solved by a sensor module, comprising a master sensor unit for sensing a first environmental parameter and a slave sensor unit for sensing a second environmental parameter. The master sensor unit and the slave sensor unit are mounted on a common substrate, and a digital bus interface is used for a communication between the master sensor unit and the slave sensor unit.

Environmental parameters to be sensed by the sensor units typically represent physical quantities of a medium in the environment of the sensor module, which medium preferably is air. Environmental parameters may for instance be relative humidity of the ambient, a temperature of the ambient of the sensor module, a target gas concentration, or a target aerosol concentration, especially a particulate matter concentration in the ambient. Specifically, the target gas may include a mixture of gases, such as volatile organic compounds, or individual gases, such as individual volatile organic compounds (e.g. ethanol, formaldehyde, isopropanol), nitrogen oxide, hydrogen, ozone, carbon monoxide, ammonia, or carbon dioxide.

Different target gases shall constitute different environmental parameters. Different target aerosols shall constitute different environmental parameters. However, also different ranges of concentration of an individual target gas or an individual aerosol shall be considered as different environmental parameters. Sensors, in particular gas sensors, having different cross sensitivities to gases other than the target gas shall be considered as sensor units sensing different environmental parameters. Particulate matters such as e.g. sensed by an optical particle counter shall constitute different environmental parameters when classified into different sizes/size ranges, e.g. of PM size 1, 2.5, 5, 10, etc., each in micrometers. The environmental parameters sensed by the master sensor unit and the one or more slave sensor units preferably are different from each other.

The common substrate may for instance be one of a circuit board, and preferably a printed circuit board, a ceramic substrate, a lead-frame to which the sensor units may be mounted and be electrically connected to, e.g. by means of bond wires, or any form of support on which the master sensor unit and the slave sensor unit can be mounted and via which the sensor units are electrically connected to each other, e.g. by means of conductors on or in the substrate.

The master sensor unit and the slave sensor unit are separate physical entities, such as two individual units, such as two individual semiconductor chips, and in particular two individual integrated circuits containing a sensor each.

While it is explicitly referred to a master sensor unit and a slave sensor unit, both the master sensor unit and the slave sensor unit may collectively be addressed as sensor units in the following.

The proposed sensor module sets up a masterslave relation between the sensor units, which makes a space-saving and compact configuration possible, since the master sensor unit is not only a control unit, but also measures a physical quantity. The master sensor unit may e.g. comprise a humidity sensor or a combined humidity and temperature sensor, wherein the temperature sensor preferably is configured and arranged to sense a temperature of the ambient of the sensor module.

At the same time, the proposed sensor module permits to use sensors with limited processing functionality and/or limited memory capacity and/or limited data availability and/or limited interface capabilities as slave sensor units—such as e.g. a MOX gas sensor, and/or an electrochemical gas sensor, e.g. for CO2, and/or an optical particle counter, e.g. for measuring an aerosol concentration, each embodied as sensor chip—without corrupting measurements of the master sensor unit or corrupting the master sensor unit itself.

Accordingly, the sensor module provides a means for detecting environmental conditions. Environmental conditions have a major impact on human's well-being, comfort, and productivity. The sensor module may provide detailed and reliable data on key environmental parameters such as humidity, temperature, volatile organic compounds (VOCs), particulate matter (PM 2.5 μm), and/or CO2. The reliable detection and evaluation of environmental parameters opens up new possibilities to create smarter devices that improve comfort and well-being of humans as well as increase energy efficiency in a wide variety of applications. Applications of the sensor module may include, for example, and without limitation: Monitoring and/or analysis of one or more of indoor air quality, outdoor air quality, ventilation air quality, or breath analysis.

In a preferred embodiment, the slave sensor unit comprises a gas sensor. Preferably, the gas sensor is embodied as one of an optical gas sensor; a photoacoustic gas sensor; a thermal gas sensor; an electrochemical gas sensor, wherein the electrochemical gas sensor preferably is one of a solid EC gas sensor or a room temperature organic liquid EC gas sensor. Preferably, in case of the MOX-based gas sensor, a target gas concentration is sensed other than $CO_2$. Preferably, in case of the optical gas sensor, a concentration of $CO_2$ is sensed. Preferably, in case of the thermal gas sensor, a target gas concentration in a high range, in particular higher than a range sensed by a MOX-based sensor, is sensed. Preferably, in case of the solid electrochemical (EC) gas sensor including a heater, a concentration of $CO_2$ is sensed. Preferably, in case of the room temperature organic liquid electrochemical (EC) gas sensor, a concentration of a target gas other than $CO_2$ is sensed, and preferably at an improved selectivity compared to a MOX-based gas sensor. In a different embodiment, the gas sensor is embodied as an aerosol concentration sensor, in particular a PM sensor, and in particular an optical particle counter. In a further embodiment, the gas sensor is a humidity sensor.

Preferably, in addition to the sensor unit, another sensor unit is provided including a sensor of the list in the above paragraph that senses a different environmental parameter than the slave sensor unit. Preferably, in addition to the sensor unit and the other sensor unit, a further sensor unit is provided including a sensor of the above list that senses a different environmental parameter than the one of the sensor unit and the other sensor unit. However, even more slave sensor units can be provided, each for sensing a different environmental parameter.

In a preferred embodiment, in a set of multiple slave sensor units at least two of those include gas sensors out of the ones listed above for sensing different environmental parameters.

The different sensor units may be, but do not need to be manufactured by equal process technologies. In particular, in case the different sensor units are manufactured by applying different process technologies, the present module is beneficial in that although different units are provided for the various sensors, a compact arrangement is achieved nevertheless. One sensor that may be manufactured by a process technology common (such as CMOS processing) or compatible (such as CMOS and MEMS processing) to the processing technology of a processor of the control unit, for example, may be integrated together with the processor and result in the master sensor unit, while a sensor preferably being manufactured by a process technology different to the one used for manufacturing the master sensor unit may be manufactured individually and only then be mounted as slave sensor unit to the common substrate together with the master sensor unit. This may facilitate development and production of versatile sensor combinations.

In a preferred embodiment, the sensor module may comprise more than one slave sensor unit, such as a set of slave sensor units, preferably wherein each slave sensor unit is configured to sense an environmental parameter different to the environmental parameters sensed by the one or more other slave sensor units of the set.

The master sensor unit comprises a non-volatile memory for storing calibration data and configuration data of the master sensor unit and the slave sensor unit. The calibration data preferably includes at least one of the data categories of the following exemplary but not limited list:
Trim data for analog circuits, for example one or more of oscillator trimming data, bias current trimming data, power-on-reset (POR) level trimming data;
Digital signal processing parameters, for example one or more of signal offset and/or gain data, look-up-tables.

The configuration data preferably includes at least one of the data categories of the following exemplary but not limited list:
Analog data path configuration data, for example one or more of sensor selection data, an analog-to-digital converter (ADC) sampling frequency;
Digital data path configuration data, for example one or more of processing step selection data, measurement sequence data;
Communication interface configuration data, for example slave sensor unit address, protocol selection data;
I/O pad configuration, for example, drive strength selection data.

Any combinations of the listed data categories within or across the calibration and configuration data group, or any combination of individual items within the data categories, or across the data categories of a common group, or across the calibration data group and the configuration data group are possible.

Preferably, the slave sensor unit does not comprise a memory for calibration and/or configuration data for its corresponding sensor element, as this data is stored in the master sensor unit. Accordingly, at least no non-volatile memory needs to be provided in the one or more slave sensor units which allows for easier integration.

For the reasons mentioned above, the master sensor unit is embodied as a first chip, and the slave sensor unit is embodied as a second chip. Each further slave sensor unit of a set of slave sensor units preferably is embodied as an individual chip, too. Preferably, the different sensor units are arranged side by side on the common substrate, and not stacked.

Preferably, the sensor module comprises a housing for the master sensor unit and the one or more slave sensor units on the common substrate. The housing may be a plastic casing or a metal casing, or in a different embodiment, it may be a moulding compound encapsulating the sensor units and the common substrate, yielding a robust sensor package. Advantageously, the housing comprises at least one opening for the sensor units in order to sense the environmental parameters fast and accurately. By means of the at least one opening, the medium to be investigated can access the respective sensor unit and the environmental parameter of the medium, such as air, can be sensed by the respective sensor unit. In different embodiments, there may be only one common opening in the housing for all sensor units, or there may be individual openings for the different sensor units.

The master sensor unit or the common substrate preferably also comprises pins for contacting the master sensor unit from externally. On the one hand, the pins are used to receive a single or multiple external power supply voltages, i.e. VDDIO. On the other hand, the master sensor unit is configured to provide and receive signals via the pins, the respective pins physically representing an interface of the sensor module to communicate with the outside, i.e. with one or more electronic units separate and external from the sensor module. Preferably, the sensor module is configured to communicate with the one or more external units exclusively via the interface for the master sensor unit, while the slave sensor units lack of any interface to such external units.

Preferably, all slave sensor units are connected to the same digital bus interface for communicating with the master sensor unit and each slave sensor unit and/or a protocol of the digital bus interface is configured to make a slave sensor unit exclusively communicate with the master sensor unit, but not with any other slave sensor unit.

Besides, the master sensor unit may be configured to receive an external time reference, in particular from a quartz crystal oscillator, and may be configured to derive a common clock for the master sensor unit and the one or more slave sensor units from the received external time reference, in particular for synchronizing the communication between the master sensor unit and the one or more slave sensor units. Synchronization in this context means that the master sensor unit and slave sensor unit/s operate on a common clock with a common clock period and common phase, wherein preferably the master sensor unit supplies the slave sensor units with the common clock. This facilitates the communication via the digital bus interface, which may e.g. be similar to an I2C interface. Alternatively, the master sensor unit may be equipped with a clock generation unit, the clock of which may also be used as a common clock for all sensor units. Preferably, the slave sensor unit does not comprise its own clock, such as a quartz. Instead, the clock for the slave sensor unit is supplied by the master sensor unit in this embodiment.

The common clock and a reset signal is preferably supplied to the at least one slave sensor unit via a combined signal over the digital bus interface on a single pin. A reset pulse may then be derived from the combined signal in the at least one slave sensor unit if the common clock period deviates from a nominal common clock period in a defined way. In this way, only the single pin is needed for transmitting the common clock and the reset signal, which is space-saving and makes the sensor module simpler.

A preferred way of defining the way in which the common clock period deviates from a nominal common clock period to cause a reset pulse is the following: The at least one slave sensor unit preferably comprises a reset sequence detector, wherein the reset sequence detector generates the reset pulse when detecting in the combined signal a high pulse that is longer than a nominal high time directly followed by a low pulse that is shorter than a nominal low time. The reset pulse is in particular generated directly at the end of the low pulse, which is the end of the so-called reset sequence made up of one longer-than-normal high pulse and one shorter-than-normal low pulse.

Such reset sequence is compatible with a "power-over-clock" scheme where a supply voltage for the at least one slave sensor unit is also transmitted with the combined signal via the digital bus interface: The combined signal over the digital bus interface is preferably additionally used to provide the supply voltage to the at least one slave sensor unit. Preferably a cumulated duration of high pulses in the combined signal is longer than a cumulated duration of low pulses. The latter condition ensures a sufficient power supply. It is, however, not implemented in usual "power-over-clock" schemes which exhibit a low voltage for most of the time. The combined signal may be low-pass filtered if suitable to allow for a more continuous power supply. Such "power-over-clock" schemes eliminates the need for another pin, namely a pin for the supply voltage.

In a preferred embodiment, the master sensor unit comprises a power management unit for generating an internal supply voltage and a supply voltage for the digital bus interface, all derived from an external supply voltage. The internal supply voltage may be used for operating the sensor as well as a processing unit of the master sensor unit. The supply voltage for the digital bus interface is used for the communication with the one or more slave sensor units. The slave sensor unit may comprise its own power management unit for generating an internal supply voltage, also derived from the common external supply voltage. The internal supply voltage in this embodiment preferably serves for powering all parts of the slave sensor unit, i.e. including analog as well as digital parts.

In a different embodiment, the powering of analog parts of the slave sensor unit remains as above, i.e. the supply voltage is derived from the common external supply voltage. However, the supply voltage for digital parts of the slave sensor unit is derived from the digital bus interface. Hence, in this embodiment, the power management unit of the master sensor unit supplies a supply voltage to the slave sensor unit via the digital bus interface.

The master sensor unit may also comprise a power-on reset generation to reset a processing unit and volatile memory, also of the slave sensor unit, to an initial state. Accordingly, the slave sensor unit does not comprise its own reset function, but is reset by the master sensor unit.

The master sensor unit may also comprise a measurement sequence unit for controlling and in particular triggering a sequence of measurements to be taken by the different sensor units. In a preferred embodiment, the sequence of measurements by the sensor units is triggered synchronously, preferably based on the common clock with the common clock period and the common phase applied by all sensor units. This means, that at each sensor unit a measurement is triggered synchronously with the clock only, i.e. based on the common clock, and of a frequency of multiple integers of the common clock period. In a preferred embodiment, the measurement sequence unit is configured to trigger measurements by all sensor units at the same time. Preferably, the slave sensor unit does not comprise its own measurement sequence unit, but is triggered to conduct measurements by the master sensor unit.

In particular, the measurement sequence unit is configured to initiate measurements of a specific sensor unit, e.g. one of the slave sensor units, dependent on a value measured by a different sensor unit, e.g. the master sensor unit. In this way, reasonable combinations of measurement values, cross-calibrations or conditional measurements, such as wake-up on alarm, are facilitated. Also, the measurement sequence unit may be configured to reduce interference between the slave sensor unit measurements, and may optimize measurement acquisition time.

Preferably, the master sensor unit comprises a processing unit for processing signals measured by the sensor units. The processing unit may be configured to combine measured signals of different sensor units yielding a processed signal. This can be particularly useful to perform averaging or a temperature compensation on a signal of a certain physical quantity based on a measured temperature value. Specifically, a temperature value measured by one of the sensor units including a temperature sensor is used to perform a temperature compensation on a signal of a different physical quantity measured by to another one of the sensor units. And/or, a relative humidity value measured by one of the sensor units may be used to perform a humidity compensation on a signal of a different physical quantity measured by another one of the sensor units.

Such processing of signals from one, two or more sensors units may be achieved through look-up tables stored in a memory of the master sensor unit.

Additionally, the master sensor unit may comprise a volatile or non-volatile memory for storing a measured signal or a processed signal of one or more of the sensor units. The stored signal can in particular be related to a time of measurement by means of adding a time stamp.

In a preferred embodiment, the master sensor unit comprises a self-test unit configured to execute a test sequence on one or more sensor units during manufacturing or application of the sensor module. The test sequence may trigger test measurements and then give an indication, which sensor unit is damaged or what defect might may have occurred, which is particularly helpful, if the sensor module comprises several different sensor units.

In one embodiment, the slave sensor unit comprises a MEMS sensor, analog front-end electronics for interfacing sensor signals, and an analog-to-digital converter. In addition to the digital bus interface, an analog interface may be provided between the master sensor unit and the slave sensor unit such that the slave sensor unit may be configured to communicate with the master sensor unit via an analog signal.

The slave sensor unit may comprise a non-volatile memory for storing a unique unit identification number for the communication. In that case, the digital bus interface may comprise a protocol to address each slave sensor unit separately. The non-volatile memory can be programmed electronically, by optical means, e.g. by laser trimming, by photolithography, or by an additive printing technology.

Preferably, the digital bus interface is a low pin-count digital interface, in particular a two-wire interface or a single-wire interface. The interface may be a bi-directional interface. The interface may as well transmit a reset signal or a common clock signal, ensuring a synchronous operation of all sensor units. Preferably, the digital bus interface provides a lossless transmission of measurement data between the slave sensor unit and the master sensor unit.

Preferably, the or each slave sensor unit of the set lacks of its own clock, such as a quartz, and lacks of its own a reset, and lacks of memory for calibration and/or configuration data, and lacks of its own measurement sequence unit for timing its measurements. Instead, all these functions are taken over by the master sensor unit which preferably implements these functions not only with respect to its own sensing element, but also with respect to the slave sensor units.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings, it is illustrated in FIG. 1 a schematic view of a sensor module according to an embodiment of the present invention, FIG. 2 a block diagram of a sensor module according to an embodiment of the present invention, FIG. 3 a block diagram of a sensor module according to an embodiment of the present invention, FIG. 4 timing of clock and measurements as used in a sensor module according to an embodiment of the present invention, FIG. 5 a combined signal for common clock and reset signal used to derive a reset pulse, and FIG. 6 a block diagram of a usage of the combined signal for the common clock, the reset pulse and a supply voltage ("power-over-clock").

DETAILED DESCRIPTION OF THE DRAWINGS

Figure 1:
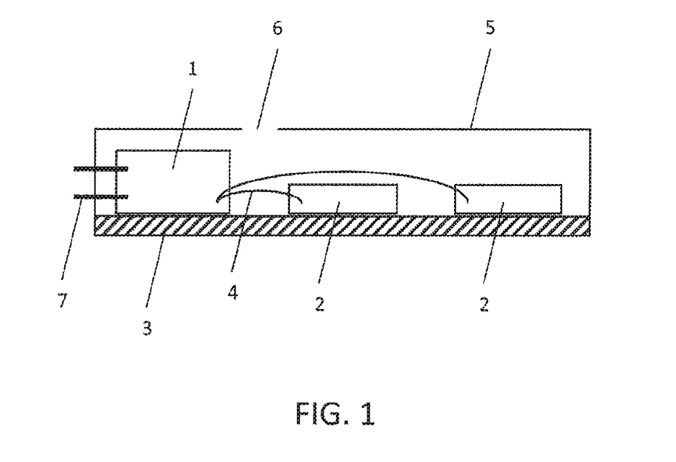

FIG. 1 shows a schematic view of a first embodiment of the sensor module with a master sensor unit 1 and two slave sensor units 2 on a common substrate 3. The master sensor unit 1 and the slave sensor units 2 are integrated in three separate chips, preferably semiconductor chips. The common substrate 3 may be a printed circuit board or any other support for mounting the chips on. The number of slave sensor units 2 may be one, two or more.

Each slave sensor unit 2 communicates with the master sensor unit 1 via a digital bus interface 4. The digital bus interface 4 is a low pin-count digital interface, preferably a two-wire or one-wire interface. The communication via the digital bus interface 4 comprises at least signals measured by the slave sensor units 2 and start/stop conditions for the measurements. It may as well comprise a clock signal for synchronizing the communication and the measurements of the master sensor unit 1 and the slave sensor units 2. The clock signal can e.g. be generated by a quartz, which may be located internal in the master sensor unit 1, or the signal of which may be supplied from external to the sensor module, and preferably to the master sensor unit 1.

The master sensor unit 1 and the slave sensor units 2 are arranged in a housing 5, which protects the chips and yields a robust sensor module. The housing 5 may be made of plastic or metal, or it may be an encapsulation, e.g. comprising a moulding compound. The housing 5 comprises at least one opening 6 for the sensor units 1, 2 to be able to sense physical quantities of an environment of the sensor module. In one embodiment, the housing 5 comprises one common opening 6 for all sensor units 1, 2. In a different embodiment, there are separate openings 6 for several or all of the sensor units 1, 2 in the housing.

The sensed physical quantities may comprise a variety of quantities, e.g. relative humidity, temperature, gas concentration or aerosol concentration, preferably all of the ambient. In a preferred embodiment, the master sensor unit 1 comprises a combined sensor for relative humidity and temperature, one slave sensor unit 2 comprises a 4-pixel MOX gas sensor, and the other slave sensor unit 2 comprises an electrochemical CO2 sensor. An extension to more slave sensor units 2 is possible, with e.g. an optical particle counter as additional slave sensor unit 2. The described setup and communication make it possible to integrate common sensor units into the sensor module as slave sensor units 2 which would otherwise be difficult or impossible to be integrated in a small package together with the sensor, a processor and a memory of the master sensor unit 1.

The master sensor unit 1 receives a power supplied from externally via one or more of pins 7. The pins 7 are also used to receive and supply control signals and measured signals and hence represent an interface for the master sensor unit 1 to communicate with an external unit. In one embodiment, the master sensor unit 1 comprises a power management unit for generating an internal supply voltage and a supply voltage for the digital bus interface 4. The internal supply voltage may also be provided to the slave sensor units 2 such that they do not necessarily require a separate power management unit.

Figure 2:
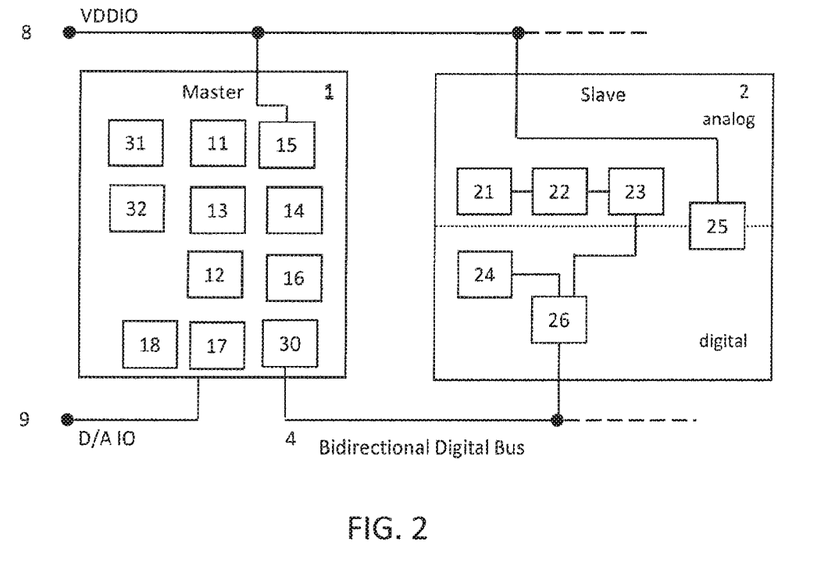

FIG. 2 shows a block diagram of a sensor module according to an embodiment of the present invention with a master sensor unit 1 and one slave sensor unit 2 as well as their respective subunits 1x, 3x for the master sensor unit 1, and 2x for the slave sensor unit 2. A possible extension to more than one slave sensor units 2 is indicated through the dashed lines at the right of FIG. 2. In this embodiment, the master sensor unit 1 and the slave sensor unit 2 are fed by a common external supply voltage 8 (VDDIO).

The master sensor unit 1 receives and transmits signals via a digital or analog input and output line 9 (D/A IO), also referred to as interface for the master sensor unit 1. The input signals may be control signals for performing specific measurement routines. The output signals may be signals of one or more physical quantities measured by the sensor units 1 and 2, or they comprise a combined or processed signal from more than one of the sensor units 1 and 2, or a control signal, such as an alarm. The master sensor unit 1 communicates with the slave sensor unit 2 via a digital bus interface 4. For this purpose, the master sensor unit 1 comprises a digital master interface 30, and the slave sensor unit comprises a digital slave interface 26.

The master sensor unit 1 may comprise an oscillator 31 for deriving a common clock from for the master sensor unit 1 and the slave sensor unit 2. The common clock signal preferably is transmitted to the slave sensor unit 2 via the digital bus interface 4. The master sensor unit 1 comprises a sensitive element 11, which may be sensitive to relative humidity and/or temperature. In a different embodiment, the sensitive element 11 is a capacitive $CO_2$ sensor. The master sensor unit 1 further comprises a non-volatile memory 12 for storing calibration data of the master sensor unit 1 and the slave sensor unit 2, and a non-volatile memory 13 for storing configuration data of both the master sensor unit 1 and the slave sensor unit 2. Non-volatile memories 12 and 13 may be represented by a common non-volatile memory having the various data stored in a common memory structure. Calibration data may be stored in the form of look-up tables which facilitate different operations on a measured signal. Accordingly, calibration data may include correcting factors for a sensor response, linearization parameters, interpolation parameters, or compensation parameters e.g. for temperature.

For processing the signals measured by the different sensor units 1, 2, the master sensor unit 1 comprises a processing unit 14, which may, for example, be a hardwired logic. The processing unit 14 is configured to perform the operations mentioned above on the measured signal, e.g. by using look-up tables provided by the non-volatile memories 12 and 13. The measured signal and/or the processed signal is stored in a memory 18.

The master sensor unit 1 additionally comprises a power management unit 15 for generating a supply voltage for the digital bus interface 4. It may also provide a supply voltage different from VDDIO for other subunits, such as the sensitive element 11.

Advantageously, the master sensor unit 1 comprises a measurement sequence unit 16 for controlling a sequence of measurements by the sensor units 1 and 2. The measurement sequence unit 16 may e.g. ensure a right order of measurements by the different sensor units 1, 2, or it may apply conditions for a specific sensor unit 1, 2 to provide a measurement value, or it may apply different sampling rates for different sensor units 1, 2.

Also, the master sensor unit 1 preferably comprises a self-test unit 17 configured to execute a test sequence on at least one sensor unit 1, 2 during manufacturing or application of the sensor module. The self-test unit 17 may apply a certain measurement routine to a specific sensor unit 1, 2, compare the measured data with a stored reference, and output a signal indicating a possible defect of the specific sensor unit 1, 2.

Preferably, the master sensor unit 1 comprises a power-on reset 32 generation to reset the processing unit 14 and/or the volatile memory 18 to an initial state.

In comparison with the master sensor unit 1, the slave sensor unit 2 is of limited functionality. It is sufficient that it comprises a MEMS sensor 21, e.g. a MOX gas sensor or an electrochemical gas sensor, analog front-end electronics 22 such as a readout for interfacing sensor signals, and an analog-to-digital converter 23. Hence, the slave sensor unit 2 may be a common MEMS chip.

Advantageously, the slave sensor unit 2 comprises a non-volatile memory 24 for storing a unique unit identification number. This facilitates addressing each slave sensor unit 2 separately via the digital bus interface 4.

The slave sensor unit 2 may also comprise a power management unit 25 for generating an internal supply voltage derived from the common external supply voltage 8 (VDDIO), for supplying power to its analog as well as its digital parts.

Figure 3:
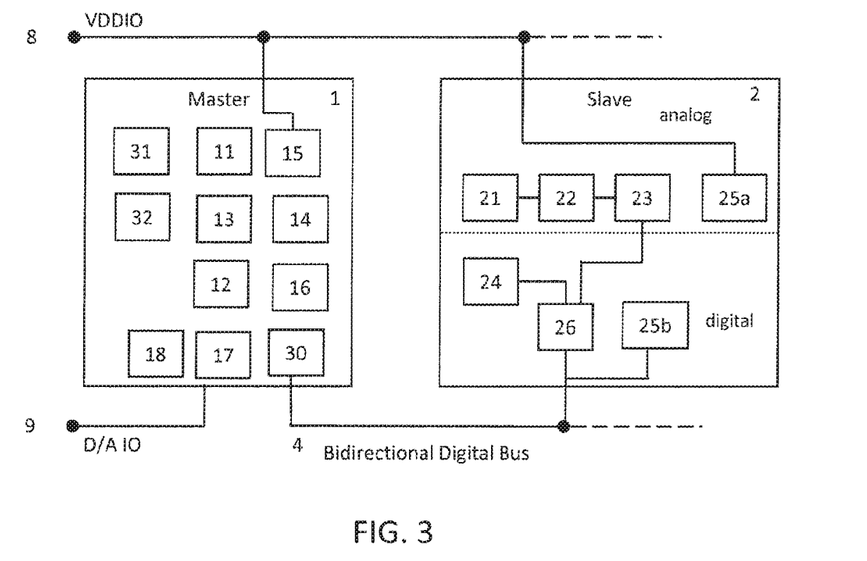

FIG. 3 illustrates a block diagram of a sensor module according to another embodiment of the present invention. The sensor module of FIG. 3 only differs from the sensor module of FIG. 2 in that the power supply in the slave sensor unit 2 is realized different. Instead of the power management unit 25 of FIG. 2 responsible for powering analog and digital parts of the slave sensor unit 2, in the embodiment of FIG. 3, a power management unit 25a is provided for generating an internal supply voltage derived from the common external supply voltage 8 (VDDIO), but limited to supplying power to the analog parts of the slave sensor unit 2 only. Instead, powering of the digital parts of the slave sensor unit 2 is achieved by means of different power management unit 25b, which derives the supply voltage for the digital parts from the digital bus interface 4. Hence, in this embodiment, the power management unit 15 of the master sensor unit 1 supplies a supply voltage—preferably different from VDDIO but derived therefrom—to the slave sensor unit 2 via the digital bus interface 4.

Figure 4:
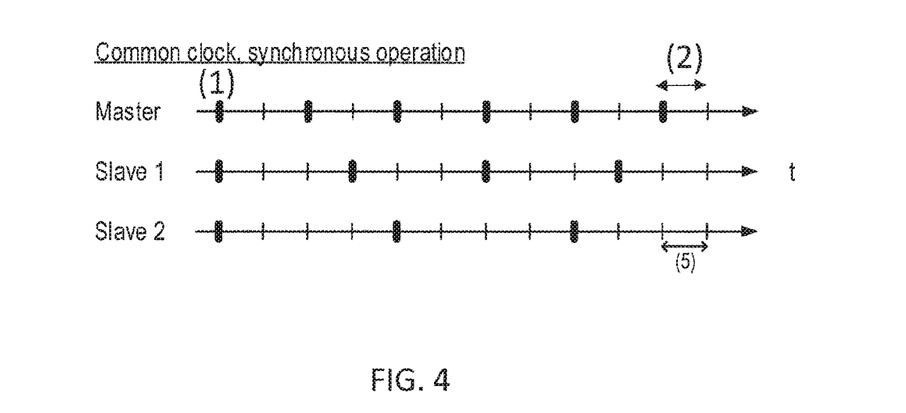

FIG. 4 illustrates the timing of clock and measurements as used in a sensor module according to an embodiment of the present invention. Such timing may be used in any of the embodiments of the sensor modules according to FIGS. 1 to 3. A clock of the master is shown in the first graph over time. The period of the clock of the master is referred to by (2). The second graph shows a clock of a first slave sensor unit, the period of which clock is equal to the period of the master clock. The third graph shows a clock of a second slave sensor unit, the period of which clock is equal to the period of the master clock and the clock of the first slave sensor unit. Accordingly, it is preferred that all sensor units, i.e. the master sensor unit and any slave sensor unit are operated under the same clock signal, i.e. are operated under a common clock with a defined common clock period (5) and a common phase: Hence, all clocks are in phase.

As to the timing of measurements triggered or taken by the individual sensor units, reference (1) indicates such points in time of measurement strobes, i.e. all bold strokes in FIG. 4 represent a measurement strobe within a sequence of measurements taken by the sensor units. Accordingly, the sensor of the master sensor unit takes measurements/is triggered by the measurement sequence unit to take measurements every second clock period. The sensor of the first slave sensor unit takes measurements/is triggered by the measurement sequence unit of the master sensor unit to take measurements every third clock period. The sensor of the second slave sensor unit takes measurements/is triggered by the measurement sequence unit of the master sensor unit to take measurements every fourth clock period. Accordingly, the measurements of the various sensors in the master sensor unit and the slave sensor units are taken synchronously, i.e. based on the common clock, and of a frequency of multiple integers of the common clock period.

Figure 5:
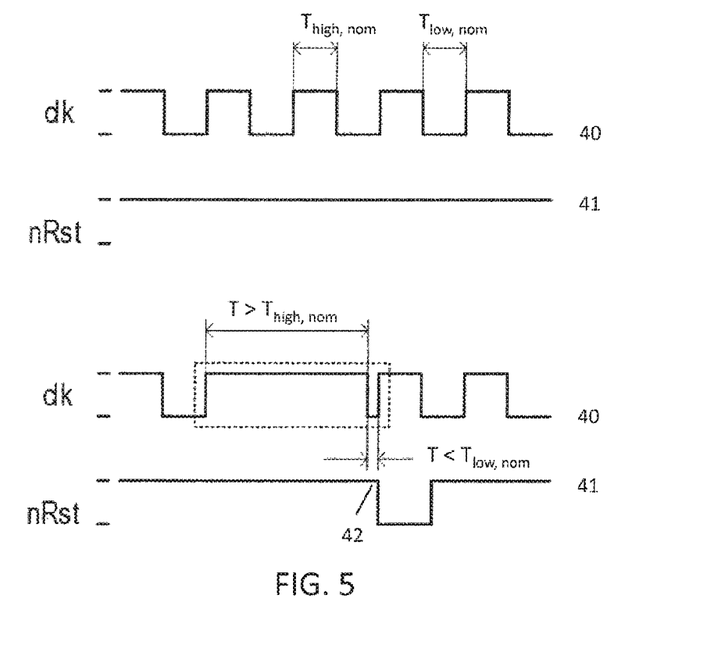

FIG. 5 shows a combined signal 40 for common clock and reset signal 41 used to derive a reset pulse 42. The combined signal 40 is supplied from the master sensor unit to any slave sensor unit via the digital interface bus. The combined signal 40 may be transmitted via a single pin, which is shared for reset and clock signals. The reset pulse for the slave sensor unit is generated on-chip if the clock timing deviates from a nominal clock timing in a specific way.

FIG. 5 depicts a possible implementation of common clock and reset signal in one combined signal. The upper part of FIG. 5 shows a situation where no reset pulse from the combined signal 40 is generated since the clock timing corresponds to the nominal clock timing with nominal high time $T_{high,nom}$ and nominal low time $T_{low,nom}$.

The lower part of FIG. 5 shows a situation where a high pulse in the combined signal 40 is longer than the nominal high time $T_{high,nom}$, and this high pulse is directly followed by a low pulse that is shorter than the nominal low time $T_{low,nom}$. Such sequence of a high pulse and a low pulse, called a reset sequence, is interpreted as a reset pulse 42, and the slave sensor unit is reset.

Figure 6:
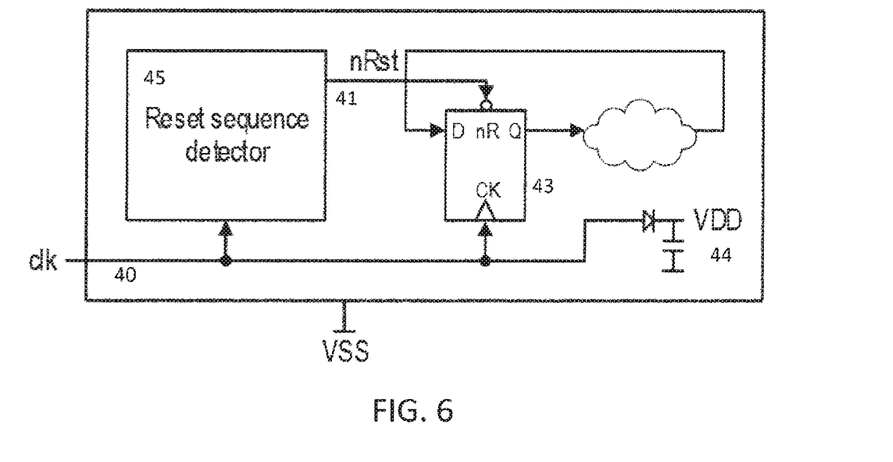

FIG. 6 shows a block diagram of a usage of the combined signal 40 for the common clock 43, the reset signal 41 and additionally a supply voltage 44. Such combination or usage of signals is also called "power-over-clock". A reset sequence detector 45 evaluates the combined signal 40 supplied to the slave sensor unit. If the reset sequence detector 45 detects a reset sequence, for instance defined as in depicted in FIG. 5, it generates a reset pulse. In addition to the common clock 43 and the reset signal 41, also the supply voltage 44 for the slave sensor unit is taken from the combined signal 40. In this way, a dedicated pin for the supply voltage is not needed. Providing the supply voltage 44 via the combined signal 40 is facilitated since the combined signal 40 is "high" for most of the time, i.e. a cumulated duration of the high pulses is longer than a cumulated duration of the low pulses. Also the reset sequence as defined above is compatible with a "power-over-clock" scheme where the supply voltage for the slave sensor unit is provided through the combined signal together with the common clock. The combined signal may be low-pass filtered for these purposes.

The invention claimed is:

1. A sensor module, comprising:
   a master sensor unit configured to sense a first environmental parameter;
   a slave sensor unit configured to sense a second environmental parameter;
   a common substrate on which the master sensor unit and the slave sensor unit are mounted; and
   a digital bus interface for a communication between the master sensor unit and the slave sensor unit,
   wherein the master sensor unit comprises a non-volatile memory configured to store calibration data and configuration data of the master sensor unit and the slave sensor unit,
   wherein the master sensor unit is embodied as a first chip, and the slave sensor unit is embodied as a second chip,
   wherein the master sensor unit and the slave sensor unit are configured to operate synchronously, based on a common clock with a common clock period and common phase for each sensor unit,
   wherein the master sensor unit is configured to supply the common clock to the slave sensor unit,
   wherein the common clock and a reset signal are supplied to the slave sensor unit via a combined signal over the digital bus interface on a single pin, and
   wherein a reset pulse is derived from the combined signal in the slave sensor unit if the common clock period deviates from a nominal common clock period in a defined way.

2. The sensor module according to claim 1, comprising a set of slave sensor units, each slave sensor unit of the set being configured to sense an environmental parameter different to the environmental parameters sensed by one or more of the other slave sensor units of the set, each slave sensor unit of the set being embodied as an individual chip.

3. The sensor module according to claim 1,
   wherein the master sensor unit is configured to receive one external time reference, from a quartz, and is configured to derive the common clock from the received external time reference.

4. The sensor module according to claim 1,
   wherein the at least one slave sensor unit comprises a reset sequence detector, and
   wherein the reset sequence detector generates the reset pulse when detecting in the combined signal a high pulse that is longer than a nominal high time directly followed by a low pulse that is shorter than a nominal low time.

5. The sensor module according to claim 1,
   wherein the combined signal over the digital bus interface is additionally used to provide a supply voltage to the slave sensor unit, and
   wherein a cumulated duration of high pulses in the combined signal is longer than a cumulated duration of low pulses.

6. The sensor module according to claim 1, wherein the master sensor unit comprising a measurement sequence unit configured to trigger a sequence of measurements by sensor units,
   wherein the measurement sequence unit is configured to trigger the sequence of measurements by the sensor units synchronously, based on the common clock applied by all the sensor units, and based on a frequency of multiple integers of the common clock period,
   wherein the measurement sequence unit is configured to trigger the measurements of all sensor units at the same time, and
   wherein the measurement sequence unit is configured to initiate measurements of a sensor unit dependent on a value measured by a different sensor unit.

7. The sensor module according to claim 1,
   comprising an interface for the master sensor unit to communicate with one or more units external to the sensor module,
   wherein the sensor module is configured to communicate with the one or more external units exclusively via the interface for the master sensor unit,
   wherein multiple slave sensor units are connected to the master sensor unit by means of the same digital bus interface,
   wherein a protocol of the digital bus interface is configured to make each slave sensor unit exclusively communicate with the master sensor unit,
   wherein the digital bus interface is a two-wire interface or a single-wire interface.

8. The sensor module according to claim 1, the master sensor unit comprising a combined humidity and temperature sensor, wherein the temperature sensor is arranged and configured to determine a temperature ambient of the sensor module.

9. The sensor module according to claim 1,
wherein the slave sensor unit comprises one of
  a gas sensor comprising one of a MOX-based gas sensor; an optical gas sensor, a photoacoustic gas sensor; a thermal gas sensor; an electrochemical gas sensor comprising a solid EC gas sensor or a room temperature organic liquid EC gas sensor;
  an aerosol concentration sensor comprising a PM optical particle counter;
  a humidity sensor;
wherein another slave sensor unit comprises one of
  a gas sensor comprising one of a MOX-based gas sensor; an optical gas sensor; a photoacoustic gas sensor; a thermal gas sensor; an electrochemical gas sensor comprising a solid EC gas sensor or a room temperature organic liquid EC gas sensor;
  an aerosol concentration sensor comprising a PM optical particle counter;
  a humidity sensor;
wherein a further slave sensor unit comprises one of
  a gas sensor comprising one of a MOX-based gas sensor; an optical gas sensor; a photoacoustic gas sensor; a thermal gas sensor; an electrochemical gas sensor comprising a solid EC gas sensor or a room temperature organic liquid EC gas sensor;
  an aerosol concentration sensor comprising a PM optical particle counter;
  a humidity sensor.

10. The sensor module according to claim 1,
comprising slave sensor units including the slave sensor unit; and a housing for the master sensor unit and the slave sensor units,
wherein the housing comprises at least one opening arranged and configured to enable a medium to access the sensor units for enabling the sensor units to sense the corresponding environmental parameters,
wherein the housing comprises at least two openings arranged and configured to enable a medium to access the sensor units for enabling the sensor units to sense the corresponding environmental parameters,
wherein the housing comprises one opening per sensor unit each opening being arranged and configured to enable a medium to access the sensor units for enabling the sensor units to sense the corresponding environmental parameters.

11. The sensor module according to claim 1,
the master sensor unit comprising a power management unit for generating an internal supply voltage and a supply voltage for the digital bus interface, and
the slave sensor unit comprising a power management unit for generating an internal supply voltage.

12. A sensor module, comprising:
a master sensor unit configured to sense a first environmental parameter;
a slave sensor unit configured to sense a second environmental parameter;
a common substrate on which the master sensor unit and the slave sensor unit are mounted; and
a digital bus interface for a communication between the master sensor unit and the slave sensor unit;
wherein the master sensor unit comprises a non-volatile memory configured to store calibration data and configuration data of the master sensor unit and the slave sensor unit,
wherein the master sensor unit is embodied as a first chip, and the slave sensor unit is embodied as a second chip,
wherein the master sensor unit and the slave sensor unit are configured to operate synchronously, based on a common clock with a common clock period and common phase for each sensor unit,
wherein the master sensor unit is configured to receive one external time reference from a quartz, and is configured to derive the common clock from the received external time reference,
wherein the master sensor unit is configured to supply the common clock to the slave sensor unit,
wherein the common clock and a reset signal are supplied to the slave sensor unit via a combined signal over the digital bus interface on a single pin, and
wherein a reset pulse is derived from the combined signal in the slave sensor unit if the common clock period deviates from a nominal common clock period in a defined way,
wherein the master sensor unit comprises a processing unit for processing signals measured by the sensor unit, the processing unit being configured to combine measured signals of different sensor units yielding a processed signal,
the processing unit being configured to use a temperature value measured by the sensor unit to perform a temperature compensation on a signal of a different physical quantity measured by another sensor unit, and/or
the processing unit being configured to use a relative humidity value measured by the sensor unit to perform a humidity compensation on a signal of a different physical quantity measured by the another slave sensor unit.

13. The sensor module according to claim 1, the master sensor unit comprising a memory for storing a measured signal or a processed signal of the sensor unit, in combination with a time stamp related to a time of the measurement.

14. The sensor module according to claim 1, the master sensor unit comprising a self-test unit configured to execute a test sequence on the sensor unit during manufacturing or application of the sensor module.

15. The sensor module according to claim 1, the slave sensor unit comprising an analog front-end electronics for interfacing sensor signals, and an analog-to-digital converter and a MEMS sensor.

16. The sensor module according to claim 1, the slave sensor unit not comprising a clock, a reset and/or memory for calibration and/or configuration data.

17. The sensor module according to claim 1, the slave sensor unit comprising a unique unit identifier, and
the digital bus interface comprising a protocol to address each of a plurality of slave sensor units separately by means of the unique unit identifier.

18. The sensor module according to claim 12,
wherein the slave sensor unit comprises a reset sequence detector,
wherein the reset sequence detector generates the reset pulse when detecting in the combined signal a high pulse that is longer than a nominal high time directly followed by a low pulse that is shorter than a nominal low time
wherein the combined signal over the digital bus interface is additionally used to provide a supply voltage to the at least one slave sensor unit, and
wherein a cumulated duration of high pulses in the combined signal is longer than a cumulated duration of low pulses.

* * * * *